United States Patent [19]

Molloy

[11] 4,001,328

[45] Jan. 4, 1977

[54] DIARYLBUTANOLAMINES

[75] Inventor: Bryan Barnet Molloy, Indianapolis, Ind.

[73] Assignee: Eli Lilly and Company, Indianapolis, Ind.

[22] Filed: June 4, 1975

[21] Appl. No.: 583,819

[52] U.S. Cl. .................. 260/567.6 M; 260/570 R; 260/247.5 R; 260/293.72; 260/326.5 C; 260/326.85; 424/330

[51] Int. Cl.² .................. C07C 91/22; C07C 91/26

[58] Field of Search ............... 260/570 R, 567.6 M

[56] References Cited

UNITED STATES PATENTS 3,395,146   7/1968   Satzinger .................. 260/570 R
3,433,836   3/1969   Petracek .................. 260/570 R

FOREIGN PATENTS OR APPLICATIONS 2,328,758   1/1975   Germany

*Primary Examiner*—Donald B. Moyer
*Attorney, Agent, or Firm*—Charles W. Ashbrook; Everet F. Smith

[57] ABSTRACT

4,4-Diphenyl-2-hydroxybutylamines are prepared by condensing amines with 1,2-epoxy-4,4-diphenylbutanes. The new compounds exist in the free base form, as acid addition salts and quaternary ammonium salts, and exhibit antiarrhythmic activity.

11 Claims, No Drawings

DIARYLBUTANOLAMINES

BACKGROUND OF THE INVENTION

There are currently available a number of drugs which are useful in the treatment of cardiac arrhythmia. No drug has yet been found, however, which is totally effective in the treatment of all types of arrhythmia. While drugs such as quinidine, procainamide, lidocaine, and digitalis, have found wide-spread success as antiarrhythmic agents, great care must be exercised in their use, due to the undesirable side effects sometimes caused by their continued use. Additionally, subjects suffering from arrhythmia sometimes become refractory to these known treatments. Consequently, additional antiarrhythmic agents are needed.

Extensive interest has recently been generated in preparing new antiarrhythmic agents as improved synthetic substitutes for the above-named drugs. Of particular importance among the new antiarrhythmic agents are the alkylenediamines described in Canadian Pat. No. 910,907.

This invention provides diarylbutanolamines which are especially useful as antiarrhythmic agents. A limited number of diarylalkanolamines are known in the prior art. For example, Blank et al., J. Med. Chem. 271–276(1969), described a variety of diphenylalkylamines, as well as a group of 3,3-diphenyl-3-hydroxypropylamines, all of which were useful as adrenocortical inhibitors. Similarly, Moffett, in U.S. Pat. No. 3,412,091, described a group of 1,1-diphenyl-2-methyl-3-(3,5-dimethylmorpholino) propanols, useful as anticonvulsants. Propranolol, 1-(isopropylamino)-3-(1-naphthyloxy)-2-propanol, has been used extensively in the treatment of cardiac arrhythmia. Recently, 4,4-diphenyl-2-hydroxybutylamines have been prepared and evaluated as antidepressive and spasmolytic agents, Dutch Pat. No. 2,328,758.

SUMMARY OF THE INVENTION

This invention relates to new diarylbutanolamine compounds that are useful as antiarrhythmic agents, and to a method for treating arrhythmia. More particularly, the present invention provides new diarylhydroxybutylamines having the formula

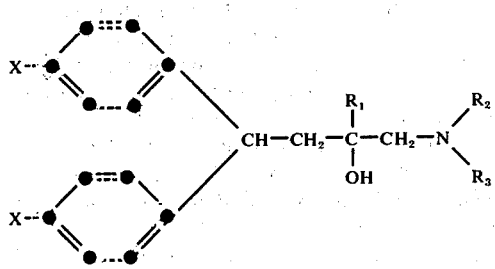

in which X is hydrogen or fluorine; $R_1$ is hydrogen or $C_1$–$C_3$ alkyl; $R_2$ and $R_3$ independently are hydrogen, $C_1$–$C_6$ alkyl or —$CH_2R_4$, in which $R_4$ is $C_2$–$C_5$ alkenyl, or $R_2$ and $R_3$ taken together with the adjacent nitrogen atom to which they are attached complete a heterocyclic ring selected from pyrrolidine, piperidine, morpholine, or methyl and dimethyl substituted pyrrolidine, piperidine and morpholine. Also included within the scope of this invention are the non-toxic pharmaceutically acceptable acid addition salts as well as quaternary ammonium salts of the compounds having the above formula. The compounds provided by this invention are particularly useful in the treatment of arrhythmia, and can be administered to a subject in need of such treatment by the oral or the parenteral route.

DETAILED DESCRIPTION OF THE INVENTION

In the above formula, $R_1$ represents hydrogen, as well as a $C_1$–$C_3$ alkyl group, examples of which include methyl, ethyl, n-propyl and isopropyl.

Examples of $R_2$ and $R_3$ when they represent a $C_1$–$C_6$ alkyl group include methyl, ethyl, n-propyl, isopropyl, n-butyl, isobutyl, tert.-butyl, n-pentyl, isopentyl, 2-methyl-butyl, n-hexyl, isohexyl, and 2,3-dimethylbutyl. Typical examples of alkenyl groups represented by $R_2$ or $R_3$ include allyl, 2-butenyl, 3-butenyl, 2-pentenyl, 4-pentenyl, 3-hexenyl, 4-hexenyl, 2-methyl-2-hexenyl, and the like.

Heterocyclic ring systems represented by $R_2$ and $R_3$ when taken together with the adjacent nitrogen atom to which they are attached include 2-methylpyrrolidine, 2,5-dimethylpyrrolidine, 2-methylpiperidine, 2,6-dimethylpiperidine, 2-methylmorpholine, and 2,6-dimethylmorpholine, as well as the non-alkylated heterocyclic rings.

As hereinbefore pointed out, the compounds of this invention can exist as free amine bases or alternatively as mon-toxic pharmaceutically acceptable salts. Among such salts are the acid addition salt formed by reaction of the free amine base with an organic or inorganic acid, as well as the quaternary ammonium salt. Examples of acid addition salts of the free amine bases prepared from inorganic acids include those prepared with acids such as hydrochloric, hydrobromic, sulfuric, nitrous, phosphoric, nitric, and related acids.

Examples of organic acids commonly used in the preparation of the non-toxic pharmaceutically acceptable salts of this invention include formic acid, acetic acid, oxalic acid, lactic acid, ascorbic acid, tartaric acid, maleic acid, fumaric acid, citric acid, succinic acid, benzoic acid, p-toluenesulfonic acid, methanesulfonic acid, adipic acid, and related acids.

When $R_2$ and $R_3$ of the above formula both are other than hydrogen, the diarylbutanolamine is a tertiary amine and can exist, in addition to the acid addition salt, as a quaternary ammonium salt. The quaternary ammonium salts are prepared by reacting a tertiary amine of the above formula with an alkylating agent such as methyl iodide, ethyl bromide, n-butyl chloride, isopropyl iodide, allyl bromide, dimethyl-sulfate, and the like. A group of especially preferred non-toxic pharmaceutically acceptable salts of this invention include the diarylbutanolaminium chlorides, bromides, oxalates, and succinates, as well as the diarylbutanolammonium methanesulfates, chlorides and bromides.

The diarylbutanolamines having the above formula can be prepared by any of a number of methods. The free bases preferably are prepared by reaction of a 1,2-epoxy-4,4-diarylbutane with an amine. Examples of epoxydiarylbutanes routinely used in the reaction include 1,2-epoxy-4,4-diphenylbutane, 1,2-epoxy-4,4-bis-(4-fluorophenyl)butane, 1,2-epoxy-4,4-diphenyl-2-methylbutane, 1,2-epoxy-4,4-diphenyl-2-n-propylbutane, 1,2-epoxy-4,4-bis-(4-fluorophenyl)-2-ethylbutane, and the like.

Examples of amines useful for preparing the free bases of the above formula include ammonia, methyl-amine, ethylamine, n-propylamine, isopropylamine, n-butylamine, 2-butenylamine, isobutylamine, n-pentylamine, 3-hexenylamine, isohexylamine, dimethylamine, diethylamine, diisopropylamine, di-n-butylamine, N-methylethylamine, N-methyl-2-butenylamine, N-ethylisopentylamine, N-isobutyl-n-butylamine, piperidine, 2-methylpiperidine, 2,6-dimethylpiperidine, morpholine, pyrrolidine, 2,6-dimethylmorpholine, and related amines.

The diarylbutanolamines of this invention typically are prepared by condensing a 1,2-epoxy-4,4-diphenylbutane and an amine at an elevated temperature of about 50° to 180° C. Generally the epoxide and the amine are reacted in the absence of an added reaction solvent, and if desired, the amine can be used in excess quantities sufficient to serve as solvent as well as reactant. If preferred, however, the epoxide and the amine can be utilized in about equimolar quantities, and an added reaction solvent such as dioxane, methanol, xylene, toluene, or the like, can be utilized. The reaction normally is complete within about 1 to 18 hours when carried out at a temperature of about 100° C. The product of the reaction can be isolated as the free amine base by simply evaporating any excess reactants or solvents. The diarylbutanolamine so formed generally does not require extensive purification; however, simple purification can readily be accomplished by methods such as distillation, chromatography, crystallization, or the like. An especially convenient method for purifying the diarylbutanolamine comprises dissolving the free amine in a suitable organic solvent such as diethyl ether or ethyl acetate, and converting the free amine into a water soluble acid addition salt by extracting the free amine from the organic solvent into an aqueous acid, such as aqueous sulfuric or hydrochloric acid for instance. Once the amine acid addition salt is dissolved in the aqueous acid solution, it is then converted back to the free amine by making the aqueous acidic solution alkaline, for instance by adding aqueous sodium hydroxide or potassium hydroxide. The free amine is insoluble in the aqueous alkaline solution and is easily extracted therefrom into a suitable water immiscible organic solvent such as diethyl ether, ethyl acetate, dichloromethane, or the like. Evaporation of the organic solvent from the extract then provides the corresponding diarylbutanolamine, which typically exists as an oil or a low melting solid.

The diarylbutanolamines of this invention can alternatively be prepared by reaction of an amine with a 4,4-diaryl-2-hydroxybutane having a readily displaceable group attached at the 1-position. Typical examples of readily displaceable groups include a halogen atom such as chlorine, bromine, or iodine, as well as groups such as p-toluenesulfonyl or methanesulfonyl. Examples of such suitably substituted 4,4-diaryl-2-hydroxybutanes include 4,4-diphenyl-2-hydroxybutyl chloride, 4,4-diphenyl-2-hydroxybutyl-p-toluenesulfonate, 4,4-bis-(4-fluorophenyl)-2-hydroxybutyl iodide, 4,4-diphenyl-2-hydroxy-2-methylbutyl bromide, and related compounds.

The reaction between an amine and a 4,4-diphenyl-2-hydroxybutane having a displaceable group at the 1-position generally is carried out by mixing the reactants in the presence of a reaction solvent. Commonly used solvents include methanol, diethyl ether, dioxane, dichloromethane, benzene, and toluene. The amine is generally utilized in excessive amounts. If desired; however, an equimolar quantity of the amine can be used, under which conditions the reaction typically is carried out in the presence of an added base to act as an acid scavenger. Routinely used bases include sodium methoxide, sodium hydride, potassium hydride, and sodium carbonate. The reaction normally is complete within about 2 to 20 hours when carried out at a temperature ranging from about 20° to 150° C. It will of course be recognized that the reaction of such a 4,4-diaryl-2-hydroxybutane derivative and an amine may actually involve the formation of a 1,2-epoxy butane as an intermediate; however, the precise reaction mechanism is not yet known with certainty.

An additional method of preparation of the diarylbutanolamines having the above formula wherein at least one of $R_2$ or $R_3$ is other than hydrogen comprises further alkylating a diarylbutanolamine of this invention. For example, a primary amine having the above formula, such as 4,4-diphenyl-2-hydroxybutylamine, can be alkylated with a common alkylating agent such as methyl bromide, allyl iodide, hexyl iodide, 3-hexenyl bromide, or the like. The amount of alkylating agent utilized in the reaction will depend upon the degree of alkylation desired. For example, reaction of a primary amine such as 4,4-diphenyl-2-hydroxy-2-methylbutylamine with about one molar equivalent of an alkylating agent, such as methyl iodide, will provide the corresponding secondary amine, for instance N-methyl-4,4-diphenyl-2-hydroxy-2-methylbutylamine. Similarly, when two molar equivalents of the alkylating reagent is utilized, the corresponding tertiary amine is formed. Additionally, primary and secondary amines of the above formula can be treated with formaldehyde and formic acid to provide the corresponding N-methyl and N,N-dimethyl derivative.

The diarylbutanolamine prepared by any of the above described methods can be isolated and recovered as a salt. Preferred salts include the acid addition salts which are readily prepared by reaction of the diarylbutanolamine with an acid. For example, the free amine can be dissolved in a suitable solvent such as diethyl ether, acetone, ethyl acetate, or the like, and a suitable acid, preferably an anhydrous acid such as hydrogen bromide gas, oxalic acid, benzoic acid, or the like, is added, either in an equimolar amount or in excess. The acid addition salt so formed normally precipitates out of solution and can be recovered by filtration. The solid salt is readily further purified, if desired, by recrystallization from solvents such as ethyl acetate, ethanol, methanol, or related solvents.

Additionally, valuable salts of the free amines of this invention are the quaternary ammonium salts, which salts can be prepared when both $R_2$ and $R_3$ of the above formula are other than hydrogen. Such quaternary ammonium salts are prepared by reacting a tertiary amine, such as N,N-diethyl-4,4-diphenyl-2-hydroxybutylamine for instance, with an alkylating agent such as methyl iodide, allyl bromide, n-butyl chloride, ethyl iodide, dimethyl sulfate, or 2-pentenyl bromide. The quaternization reaction typically is accomplished by commingling approximately equimolar quantities of the tertiary amine and the alkylating agent in an unreactive solvent such as acetone, methyl ethyl ketone, or benzene. Like the above-described diarylbutanolamine acid addition salts, the quaternary ammonium salts are characteristically highly crystalline solids and are readily isolated by filtration.

As already pointed out, the preferred process for preparing the diarylbutanolamines of this invention is by reaction of an amine with a 1,2-epoxy-4,4-diarylbutane. All of the amines required for the condensation reaction are well known and generally are readily available from commercial sources. The 1,2-epoxy-4,4-diarylbutanes which are required for the process are conveniently prepared by routine procedures, starting from readily available chemicals. The epoxides typically are prepared by epoxidation of a diarylbutene. Such epoxidation is customarily accomplished by treating a 4,4-diaryl-1-butene with an oxidizing agent, which generally is an organic peracid oxidizing agent. Examples of routinely used peracids include perbenzoic acid, m-chloroperbenzoic acid, peracetic acid, peroxy trifluoroacetic acid, performic acid, monoperphthalic acid, and the like. Generally, the diarylbutene and the peracid are utilized in approximately equimolar quantities, and the reaction typically is carried out in a solvent such as chloroform, dichloromethane, or benzene.

The diarylbutenes required as starting materials in the preparation of the corresponding diarylbutyl epoxides are readily prepared by routine procedures. For example, a diarylmethane can be converted to the corresponding diarylmethyl salt by reaction with a strong base such as sodium hydride, sodium amide, or potassium tert.-butoxide. The salt so formed is then reacted with a suitable propenyl alkylating agent, such as 2-propenyl chloride or 2-methyl-2-propenyl bromide for instance. The reaction is best carried out in a suitable solvent, such as an alcohol, liquid ammonia, benzene, or the like. The diarylbutene so formed is conveniently isolated by simply removing the reaction solvent, and normal purification such as distillation is sufficient.

The 1,2-epoxy-4,4-diarylbutane starting materials can alternatively be prepared by reaction of dimethylsulfonium methylide or dimethyloxosulfonium methylide with an appropriate diarylalkyl aldehyde or a diarylalkyl ketone. For example, reaction of an aldehyde such as 3,3-diphenylpropanal with either dimethylsulfonium methylide or dimethyloxosulfonium methylide in approximately equimolar amounts provides 1,2-epoxy-4,4-diphenylbutane. Similarly, reaction of a diarylalkyl ketone such as methyl-(2,2-diphenylethyl) ketone with either dimethylsulfonium methylide or dimethyloxosulfonium methylide provides 1,2-epoxy-4,4-diphenyl-2-methylbutane. Such reactions typically are carried out in a solvent such as dimethyl sulfoxide or tetrahydrofuran, and normally at a reduced temperature of about 0° C. Dimethylsulfonium methylide is prepared by reaction of trimethylsulfonium iodide with methylsulfinylcarbanion, while dimethyloxosulfonium methylide is prepared by reaction of trimethyloxosulfonium iodide with sodium hydride. Such reactions are more fully discussed by Corey et al., *J. Am. Chem. Soc.*, 84, 867(1962) and *J. Am. Chem. Soc.*, 84, 3782 (1962).

The new compounds provided by this invention are 4,4-diphenyl-2-hydroxy-butylamines. Illustrative examples of such compounds include the following:
  N-isopropyl-4,4-diphenyl-2-hydroxybutylamine
  N-isopropyl-N-methyl-4,4-diphenyl-2-hydroxybutylamine
  N-isopropyl-N-methyl-4,4-diphenyl-2-hydroxybutylamine
  N-ethyl-N-methyl-4,4-diphenyl-2-hydroxybutylamine
  N-n-hexyl-4,4-diphenyl-2-hydroxybutylamine
  N-(3-methylpentyl)-4,4-diphenyl-2-hydroxybutylamine
  N,N-diisopentyl-4,4-bis-(4-fluorophenyl)-2-hydroxybutylamine
  N-tert. butyl-4,4-bis-(4-fluorophenyl)-2-hydroxybutylamine
  N-ethyl-N-propyl-4,4-diphenyl-2-hydroxy-2-ethylbutylamine
  N-methyl-4,4-diphenyl-2-hydroxy-2-isopropylbutylamine
  N-isopropyl-4,4-bis-(4-fluorophenyl)-2-methylbutylamine
  N-allyl-N-methyl-4,4-diphenyl-2-hydroxybutylamine
  N-isopropyl-4,4-diphenyl-2-hydroxybutylaminium chloride
  N,N-diethyl-4,4-diphenyl-2-hydroxybutylaminium nitrate
  N-tert.-butyl-4,4-diphenyl-2-hydroxybutylaminium tetrafluoroborate
  N,N-diisopropyl-4,4-bis-(4-fluorophenyl)-2-hydroxy-2-methylbutylaminium perchlorate
  N-ethyl-N-methyl-N-propyl-4,4-diphenyl-2-hydroxybutylammonium chloride
  N,N,N-tri-n-butyl-4,4-diphenyl-2-hydroxy-2-methylbutylammonium bromide
  N-(3-butenyl)-N,N-dimethyl-4,4-bis-(4-fluorophenyl)-2-hydroxybutylammonium hydroxide
  N,N,N-triethyl-4,4-diphenyl-2-hydroxy-2-isopropylbutylammonium acetate
  N,N-dimethyl-N-isopropyl-4,4-diphenyl-2-hydroxybutylammonium methanesulfate
  1-(4,4-diphenyl-2-hydroxybutyl)pyrrolidine
  1-[4,4-bis-(4-fluorophenyl)-2-hydroxybutyl]piperidine
  1-(4,4-diphenyl-2-hydroxy-2-methylbutyl)-2-methylpiperidine
  1-(4,4-diphenyl-2-hydroxybutyl)-2,6-dimethylpiperidinium chloride
  1-(4,4-diphenyl-2-hydroxybutyl)-1-methylpiperidinium methanesulfate
  1-(4,4-diphenyl-2-hydroxybutyl)morpholine
  1-[4,4-bis-(4-fluorophenyl)-2-hydroxy-2-methylbutyl]morpholinium bromide
  1-(4,4-diphenyl-2-hydroxy-2-propylbutyl)-1-methylmorpholinium methanesulfate
  1-(4,4-diphenyl-2-hydroxybutyl)-1-allylmorpholinium bromide and
  1-(4,4-diphenyl-2-hydroxybutyl)-2,5-dimethyl pyrrolidinium formate As hereinabove pointed out, the new diarylbutanolamines of this invention are especially useful in the treatment of arrhythmia. A number of the compounds described herein have been evaluated as antiarrhythmic agents in dogs. In a typical experiment to determine antiarrhythmic activity attributable to the compound of this invention, mongrel dogs of either sex were anesthetized with pentobarbital. The dogs were then administered a dose of ouabain effective to induce an experimental arrhythmia. Each dog was monitored by electrocardiogram. A dose of the diarylbutanolamine of this invention sufficient to convert the arrhythmia to a normal sinus rhythm was administered by intravenous infusion. The degree of antiarrhythmic activity possessed by the diarylbutanolamine of this invention was indicated by the amount of compound required to convert the experimental arrhythmia to a normal sinus rhythm and the duration of the conversion.

The diarylbutanolamine antiarrhythmic agents provided by this invention can be administered to a subject suffering from an arrhythmia and in need of treatment, or to a subject suspected of developing an arrhythmia and in need of prophylactic treatment. Administration to a subject can be accomplished by either the oral or the parenteral route. The diarylbutanolamine can be suitably formulated with any of a number of common pharmaceutical excipients, carriers, diluents, and the like. The formulation generally takes a form which is suitable for convenient administration by the route of choice. For instance, for oral administration, the compound is typically formulated with carriers such as lactose, dextrose, mannitol, propylene glycol, calcium silicate, potato starch, or the like. Such formulations typically are molded into tablets or encapsulated into empty gelatin capsules, or alternatively dissolved as solutions, gelatin capsules, or alternatively dissolved as solutions, elixirs, or syrups. The non-toxic pharmaceutically acceptable salts of the invention are particularly suited to formulation for oral administration in a solid form such as a tablet or capsule.

The diarylbutanolamine of the invention can additionally be formulated for parenteral administration, which route is sometimes preferred for subjects suffering from a life-threatening arrhythmia. Parenteral administration can be accomplished, for example, by intravenous administration or intramuscular administration. Typically, the active ingredient will be admixed with a suitable diluent such as mannitol, sorbitol, dextrose, or saline solution. The pharmaceutical composition can be enclosed in a ampoule ready for administration, or alternatively, the composition can be diluted just prior to use by the addition of a suitable diluent, such as sterile water or the like, to the ingredients of the ampoule.

A typical pharmaceutical composition for intravenous administration will include a diarylbutanolamine of this invention, such as N-isopropyl-4,4-diphenyl-2-hydroxybutylamine. The drug will be in the amount of about 50 to 2000 mg. admixed with a suitable carrier such as five percent aqueous glucose or dextrose, or one percent saline solution for example. The solution will be made up in the amount of about 50 to 100 ml. of volume. Such a solution can be administered dropwise over a period of from 5 to 60 minutes to a subject suffering from an arrhythmia. Oral administration of a compound of this invention suitably formulated for such can then be initiated as maintenance therapy.

The diarylbutanolamine of the present invention generally is formulated in such a way that the effective dose of active ingredient being administered generally is an amount effective for treating the arrhythmia, which effective amount typically ranges from about 50 to 2000 mg. per day. A normal dose for oral administration, for instance, will contain from about 100 to 300 mg. of a diarylbutanolamine such as N-isopropyl-4,4-diphenyl-2-hydroxy-2-methyl-butylamine, preferably as the hydrochloride acid addition salt. It will of course be recognized that the precise dose being administered to a subject will depend upon the particular condition of the subject being treated and the route selected for administration.

In order to more fully understand particular aspects of this invention, the following preparation of intermediates and detailed examples of the preparation of specific diarylbutanolamines are presented. The following examples are intended to be representative only, and in no way should be construed as limiting the instant invention to any particular aspect presented hereinafter.

PREPARATION 1

Preparation of 4,4-diphenyl-1-butene

A solution of 1.5 l. of liquid ammonia containing 19.5 g. of sodium amide was stirred while a solution of 84.1 g. of diphenylmethane dissolved in 200 ml. of diethyl ether was added dropwise over about 30 minutes. The reaction mixture was stirred for 45 minutes after the addition was completed. A solution of 60.5 g. of 3-bromo-1-propene in 50 ml. of diethyl ether was then added to the reaction mixture, after which time the mixture was stirred for twelve hours. A saturated aqueous solution of ammonium chloride was then added to the reaction mixture, followed by the addition of 500 ml. of water. The product was extracted from the aqueous reaction mixture into diethyl ether. The ethereal extracts were combined, washed, and dried. Evaporation of the solvent under reduced pressure provided 93.2 g. of the product as an oil. Distillation of the crude oil afforded 4,4-diphenyl-1-butene, B.P. 95°–98° C 0.10 torr.

Analysis Calc. for $C_{16}H_{16}$.
Theory: C, 92.26; H, 7.74.
Found: C, 92.41; H, 7.76.

PREPARATIONS 2–3

Following the procedure set forth in Preparation 1, the following diarylbutenes were prepared from the corresponding diarylmethane and a haloalkene.

4,4-Diphenyl-2-methyl-1-butene

B.P. 91°–94° C; 0.03 torr.

4,4-Bis-(4-fluorophenyl)-1-butene

B.P. 94°–100° C; 0.04 torr.

PREPARATION 4

1,2-Epoxy-4,4-diphenylbutane

A solution of 96.2 g. of 4,4-diphenyl-1-butene dissolved in 400 ml. of chloroform was added dropwise over one hour to a cold (0° C) suspension of 110.0 g. of m-chloroperbenzoic acid in 700 ml. of chloroform. The reaction mixture was warmed to about 25° C. and stirred for four hours. The reaction mixture was then washed with aqueous 2N sodium hydroxide solution, with water, and dried. Evaporation of the solvent under reduced pressure provided 158.3 g. of a yellow oil as the crude product. The oil was distilled to afford 1,2-epoxy-4,4-diphenyl-butane. B.P. 124°–126° C at 0.03 torr.

PREPARATIONS 5–6

Similarly prepared from the corresponding diarylbutene were the following epoxides.

1,2-Epoxy-2-methyl-4,4-diphenylbutane. B.P. 124°–128° C. at 0.05 torr.

1,2-Epoxy-4,4-bis-(4-fluorophenyl)butane.
nmr (CDCl$_3$): δ 2.87 (1H,m,C$_2$—H).

EXAMPLE 1

N,N-Di-n-propyl-4,4-diphenyl-2-hydroxybutylamine

A mixture of 6.73 g. of 1,2-epoxy-4,4-diphenylbutane and 30 ml. of di-n-propylamine was heated to 100° C with agitation for 12 hours. The reaction mixture was cooled to about 30° C. and concentrated under reduced pressure to provide 9.0 g. of an oil as the crude product. The oil was purified by dissolving it in 250 ml. of diethyl ether and extracting the product into 2N hydrochloric acid solution. The aqueous acidic extracts were combined, cooled, and made alkaline by the addition of 5N sodium hydroxide solution. The alkaline solution was extracted several times with fresh diethyl ether. The ethereal extracts were combined, washed with water, and dried. Evaporation of the solvent under reduced pressure provided 5.7 g. of N,N-di-n-propyl-4,4-diphenyl-2-hydroxybutylamine as an oil.

Analysis Calc. for $C_{22}H_{31}NO$ (325.496).
Theory: C, 81.18; H, 9.60; N, 4.30.
Found: C, 81.31; H, 9.33; N, 4.59.

EXAMPLE 2

N,N-Di-n-propyl-4,4-diphenyl-2-hydroxybutylaminium oxalate

The N,N-di-n-propyl-4,4-diphenyl-2-hydroxybutylamine from Example 1 above was dissolved in 50 ml. of ethyl acetate and oxalic acid was added to the solution. The precipitated product was collected by filtration and was recrystallized from ethyl alcohol. Colorless crystalline N,N-di-n-propyl-4,4-diphenyl-2-hydroxybutylaminium oxalate was collected by filtration and dried. M.P. 121°–122° C.

Analysis Calc. for $C_{24}H_{33}NO_5$ (415.53).
Theory: C, 69.37; H, 8.01; N, 3.37.
Found: C, 69.17; H, 7.91; N, 3.64.

EXAMPLE 3

N,N-Diisopropyl-4,4-diphenyl-2-hydroxybutylamine

A mixture of 11.1 g. of 1.2-epoxy-4,4-diphenylbutane and 50 ml. of diisopropylamine was agitated and heated at 160° C. for 10 hours. The reaction mixture was then cooled and concentrated under reduced pressure to provide 12.7 g. of the product as a crude oil. The oil so obtained was further purified by acid and base extraction, as described in Example 1 above. Evaporation of all solvents under reduced pressure afforded 7.5 g. of N,N-diisopropyl-4,4-diphenyl-2-hydroxybutylamine as an oil which later solidified upon standing. M.P. 55°–59° C.

Analysis Calc. for $C_{22}H_{31}NO$ (325.496)
Theory: C, 81.18; H, 9.60; N, 4.30.
Found: C, 81.16; H, 9.42; N, 4.50.

EXAMPLE 4

N-Isopropyl-4,4-diphenyl-2-hydroxybutylaminium chloride

A mixture of 10.5 g. of 1,2-epoxy-4,4-diphenylbutane and 50 ml. of isopropylamine was heated at 100° C. and agitated for 12 hours. After cooling to room temperature, the mixture was concentrated to dryness under reduced pressure to provide 13.1 g. of an oil which solidified. The N-isopropyl-4,4-diphenyl-2-hydroxybutylamine so formed was dissolved in 500 ml. of diethyl ether, to which was added excess hydrogen chloride gas. The solid precipitate was collected by filtration and recrystallized from ethyl acetate and methanol, affording 12.6 g. of N-isopropyl-4,4-diphenyl-2-hydroxybutylaminium chloride. M.P. 187°–189° C.

Analysis Calc. for $C_{19}H_{26}ClNO$ (319.876).
Theory: C, 71.34; H, 8.19; N, 4.38; Cl, 11.08.
Found: C, 71.63; H, 8.19; N, 4.47; Cl, 11.16.

EXAMPLES 5–13

Following the procedures set forth in Examples 1–4 above, the following compounds were prepared from 1,2-epoxy-4,4-diphenylbutane and the respective amine and salt forming agent.

N,N-Diisopropyl-4,4-diphenyl-2-hydroxybutylaminium oxalate

M.P. 140°–142° C.
Analysis Calc. for $C_{24}H_{33}NO_5$ (415.53).
Theory: C, 69.37; H, 8.01; N, 3.37.
Found: C, 69.53; H, 7.96; N, 3.49.

N-n-propyl-4,4-diphenyl-2-hydroxybutylaminium chloride

M.P. 135°–137° C.
Analysis Calc. for $C_{19}H_{26}ClNO$ (319.876).
Theory: C, 71.34; H, 8.19; N, 4.38; Cl, 11.08.
Found: C, 71.20; H, 7.99: N, 4.21; Cl, 10.98.

N,N-Diethyl-4,4-diphenyl-2-hydroxybutylaminium oxalate

M.P. 97°–110° C.
Analysis Calc. for $C_{22}H_{29}NO_5$ (387.476).
Theory: C, 68.20: H, 7.54; N, 3.61.
Found: C, 68.40; H, 7.25; N, 3.70.

N,N-Diethyl-4,4-diphenyl-2-hydroxybutylamine

Analysis Calc. for $C_{20}H_{27}NO$ (297.442)
Theory: C, 80.76; H, 9.15; N, 4.71.
Found: C, 80.95; H, 9.18; N, 4.60.

N,N-Dimethyl-4,4-diphenyl-2-hydroxybutylaminium chloride

M.P. 227°–230° C.
Analysis Calc. for $C_{18}H_{24}ClNO$ (305.849).
Theory: C, 70.69; H, 7.91; N, 4.58; Cl, 11.59.
Found: C, 70.62; H, 7.65; N, 4.66; Cl, 11.80.

N-Ethyl-4,4-diphenyl-2-hydroxybutylaminium chloride
M.P. 158°–160° C.

Analysis Calc. for $C_{18}H_{24}ClNO$ (305.849).
Theory: C, 70.69; H, 7.91; N, 4.58; Cl, 11.59.
Found: C, 70.55; H, 7.66; N, 4.59; Cl, 11.84.

N-Methyl-4,4-diphenyl-2-hydroxybutylaminium chloride

M.P. 181°–183° C.
Theory: C, 69.97; H, 7.60; N, 4.80; Cl, 12.15.
Found: C, 69.74; H, 7.39; N, 4.58; Cl, 12.05.

4,4-Diphenyl-2-hydroxybutylaminium chloride

M.P. 234°–236° C.
Analysis Calc. for $C_{16}H_{20}ClNO$ (277.795).
Theory: C, 69.18; H, 7.26; N, 5.04; Cl, 12.76.
Found: C, 69.21; H, 7.02; N, 4.99; Cl, 12.73.

N-tert.-butyl-4,4-diphenyl-2-hydroxybutylaminium chloride

M.P. 187°–190° C.
Analysis Calc. for $C_{20}H_{28}ClNO$ (333.903).
Theory: C, 71.94; H, 8.45; N, 4.19; Cl, 10.62.
Found: C, 7174; H, 8.47; N, 4.37; Cl, 10.90.

EXAMPLE 14

1-(4,4-diphenyl-2-hydroxybutyl)piperidinium chloride

A mixture of 6.73 g. of 1,2-epoxy-4,4-diphenylbutane and 30 ml. of piperidine was heated at 100° C. and agitated for 12 hours. The reaction mixture was cooled to room temperature and concentrated under reduced pressure to provide 9.4 g. of the desired product as a crude oil. The oil was dissolved in 300 ml. of diethyl ether, to which was added excess hydrogen chloride gas. The precipitate which formed was collected by filtration and recrystallized from ethyl acetate and methyl alcohol, affording 1-(4,4-diphenyl-2-hydroxybutyl) piperidinium chloride as colorless crystals. M.P. 195°–197° C.

Analysis Calc. for $C_{21}H_{28}ClNO$ (345.914).
Theory: C, 72.92; H, 8.16; N, 4.05; Cl, 10.25.
Found: C, 72.64; H, 8.05; N, 3.81; Cl, 10.40.

EXAMPLE 15–16

Following the procedure set forth in Example 14, the following compounds were prepared from 1,2-epoxy-4,4-diphenylbutane and the respective cyclic amine.

1-(4,4-diphenyl-2-hydroxybutyl)-2-methyl-piperidinium chloride

M.P. 131°–134° C.
Analysis Calc. for $C_{22}H_{30}ClNO$ (359.941).
Theory: C, 73.41; H, 8.40; N, 3.89; Cl, 9.85.
Found: C, 73.31; H, 8.28; N, 3.99; Cl, 10.02.

1-(4,4-diphenyl-2-hydroxybutyl)-2,6-dimethylpiperidine

B.P. 75°–195° C. 10.03 torr.
Analysis Calc. for $C_{23}H_{31}NO$ (337.507).
Theory: C, 81.85; H, 9.26; N, 4.15;
Found: C, 81.60; H, 8.99; N, 4.26.

EXAMPLE 17

N-Isopropyl-4,4-bis-(4-fluorophenyl)-2-hydroxybutylaminium chloride

A mixture of 27.9 g. of 1,2-epoxy-4,4-bis-(4-fluorophenyl)butane and 100 ml. of isopropylamine was agitated for 12 hours at 100° C. The reaction mixture was cooled to room temperature and the excess amine was removed by evaporation under reduced pressure, leaving 32.1 g. of an oil as the crude product. The oil was further purified by acid and base extraction as described in Example 1, and after removal of all solvents under reduced pressure, the oily product was dissolved in diethyl ether, to which was added hydrogen chloride gas. The precipitate which formed was collected by filtration and recrystallized from acetone and methyl alcohol, affording N-isopropyl-4,4-bis(4-fluorophenyl)-2-hydroxybutylaminium chloride as colorless needles. M.P. 187°–189° C.

Analysis Calc. for $C_{19}H_{24}F_2ClNO$ (355.857).
Theory: C, 64.13; H, 6.80; N, 3.94; F, 10.68.
Found: C, 64.12; H, 66.68; N, 3.89; F, 10.68.

EXAMPLE 18

N-Isopropyl-4,4-diphenyl-2-hydroxy-2-methyl-butylaminium chloride

A mixture of 7.5 g. of 1,2-epoxy-4,4-diphenyl-2-methylbutane and 50 ml. of isopropylamine was agitated and heated at 100° C. for 10 hours. After cooling the reaction mixture to room temperature, the excess isopropylamine was evaporated under reduced pressure, leaving 8.1 g. of an oil as the crude product. The oil was purified by acid and base extraction, and then treated with hydrogen chloride gas to obtain N-isopropyl-4,4-diphenyl-2-hydroxy-2-methyl-butylaminium chloride M.P. 139°–142° C.

Analysis Calc. for $C_{20}H_{28}ClNO$ (333.903).
Theory: C, 71.94; H, 8.45; N, 4.19; Cl, 10.62.
Found: C, 71.31; H, 8.47; N, 4.87; Cl, 9.66.

EXAMPLE 19

N,N,N-Trimethyl-4,4-diphenyl-2-hydroxybutylammonium methanesulfate

A solution of 1.61 g. of N,N-dimethyl-4,4-diphenyl-2-hydroxybutylamine in 30 ml. of benzene was stirred at ambient temperature while 0.57 ml. of dimethylsulfate was added in one portion. The reaction mixture was stirred for 12 hours, and the colorless precipitated solid was then collected by filtration and dried, providing 2.2 g. of N,N,N-trimethyl-4,4-diphenyl-2-hydroxybutylammonium methanesulfate. M.P. 150°–153° C.

Analysis Calc. for $C_{20}H_{29}NO_5S$ (395.518). Theory: C. 60.74; H, 7.39; N, 3.54.
Found: C, 60.35; H, 7.26; N, 3.46.

EXAMPLE 20

N-Allyl-N,N-dimethyl-4,4-diphenyl-2-hydroxybutylammonium bromide

A solution of 1.61 g. of N,N-dimethyl-4,4-diphenyl-2-hydroxybutylamine and 0.52 ml. of allyl bromide in 30 ml. of benzene was stirred and heated at reflux for 12 hours. The reaction mixture was cooled to room temperature, and the product crystallized. The crystallized product was collected by filtration and dried to afford 2.3 g. of N-allyl-N,N-dimethyl-4,4-diphenyl-2-hydroxy-butylammonium bromide. M.P. 113°–116° C.

Analysis Calc. for $C_{21}H_{28}BrNO$ (390.365).
Theory: C, 64.61; H, 7.23; N, 3.59; Br, 20.47.
Found: C, 64.64; H, 7.02: N, 3.58; Br, 20.33.

I claim:
1. The compound of the formula

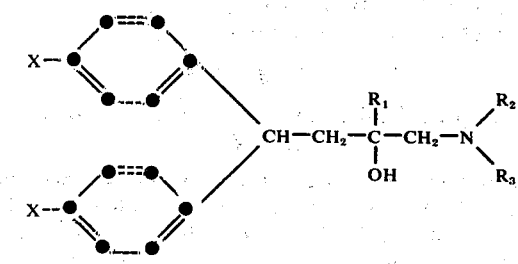

wherein:
X is hydrogen or fluorine;
$R_1$ is hydrogen or $C_1$-$C_3$ alkyl;
$R_2$ and $R_3$ independently are hydrogen, $C_1$-$C_6$ alkyl, or —$CH_2R_4$, wherein $R_4$ is $C_2$-$C_5$ alkenyl; and the non-toxic pharmaceutically acceptable salts thereof.

2. The compound of claim 1 wherein $R_2$ is other than hydrogen.

3. The compound of claim 2 wherein $R_1$ is $C_1$ -$C_3$ alkyl.

4. The compound of claim 3, said compound being N-isopropyl-4,4-diphenyl-2-hydroxy-2-methylbutylamine.

5. The compound of claim 2 wherein $R_1$ is hydrogen.

6. The compound of claim 5, said compound being N-isopropyl-4,4-diphenyl-2-hydroxybutylamine 7. The compound of claim 5, said compound being N-tert.-butyl-4,4-diphenyl-2-hydroxybutylamine.

8. The compound of claim 5, said compound being N,N-diisopropyl-4,4-diphenyl-2-hydroxybutylamine.

9. The compound of claim 5, said compound being N,N-diethyl-4,4-diphenyl-2-hydroxybutylamine.

10. The compound of claim 5, said compound being N-isopropyl-4,4-diphenyl-2-hydroxybutylaminium chloride.

11. The compound of claim 5, said compound being N,N-dimethyl-N-n-propyl-4,4-diphenyl-2-hydroxybutylammonium methanesulfate.

* * * * *